(12) United States Patent
Hartley

(10) Patent No.: US 7,976,575 B2
(45) Date of Patent: Jul. 12, 2011

(54) CURVE FORMING APPARATUS AND CURVABLE STENT GRAFT

(75) Inventor: David Ernest Hartley, Wannanup (AU)

(73) Assignees: William A. Cook Australia Pty. Ltd., Queensland (AU); Cook Medical Technologies LLC, Bloomington, IN (US)

( * ) Notice: Subject to any disclaimer, the term of this patent is extended or adjusted under 35 U.S.C. 154(b) by 338 days.

(21) Appl. No.: 12/378,131

(22) Filed: Feb. 11, 2009

(65) Prior Publication Data

US 2009/0216308 A1    Aug. 27, 2009

Related U.S. Application Data

(60) Provisional application No. 61/065,329, filed on Feb. 11, 2008, provisional application No. 61/065,535, filed on Feb. 13, 2008.

(51) Int. Cl.
*A61F 2/06* (2006.01)
(52) U.S. Cl. ...................................... 623/1.11; 623/1.13
(58) Field of Classification Search ................. 623/1.11, 623/1.12, 1.13, 1.35; 606/108, 191, 192, 606/194, 198
See application file for complete search history.

(56) References Cited

U.S. PATENT DOCUMENTS

| | | | |
|---|---|---|---|
| 5,035,706 A * | 7/1991 | Giantureo et al. | 606/198 |
| 6,974,471 B2 | 12/2005 | Van Schie et al. | |
| 2005/0049674 A1 * | 3/2005 | Berra et al. | 623/1.13 |

FOREIGN PATENT DOCUMENTS

| | | |
|---|---|---|
| EP | 0897699 | 2/1999 |
| EP | 1177779 A2 * | 2/2002 |
| WO | WO 2004/045450 | 6/2004 |

OTHER PUBLICATIONS

Int'l Search Report PCT/US2009/000871, May 29, 2009, EPO.
Written Opinion PCT/US2009/000871, May 29, 2009, EPO.

* cited by examiner

*Primary Examiner* — Gary Jackson
*Assistant Examiner* — Michael G Mendoza
(74) *Attorney, Agent, or Firm* — Richard J. Godlewski

(57) ABSTRACT

A stent graft delivery arrangement for a stent graft (50) has a proximal end to be deployed into a patient in use and a distal end to remain outside the patient. The stent graft (50) is a tubular body of a biocompatible graft material with a plurality of self expanding stents (54). The stent graft is releasably retained onto the delivery device (132) towards the proximal end thereof. A curve forming arrangement (56) on the stent graft is arranged to curve a portion of the stent graft towards its proximal end. A pulling arrangement (58) extends along the delivery device. The pulling arrangement releasably engages the curve forming arrangement such that pulling on the pulling arrangement causes the a curve forming arrangement on the stent graft to form a curve in a portion of the stent graft towards the proximal end. The pulling arrangement can be subsequently released leaving the curve forming apparatus in place on the stent graft and the portion of the stent graft towards the proximal end thereof being laterally curved. The curve forming arrangement can comprise a suture thread. A gripping arrangement engages the suture thread between the second position and the third position to prevent re-extension of the suture thread after retraction thereof. The gripping arrangement can be a slip knot (107).

10 Claims, 4 Drawing Sheets

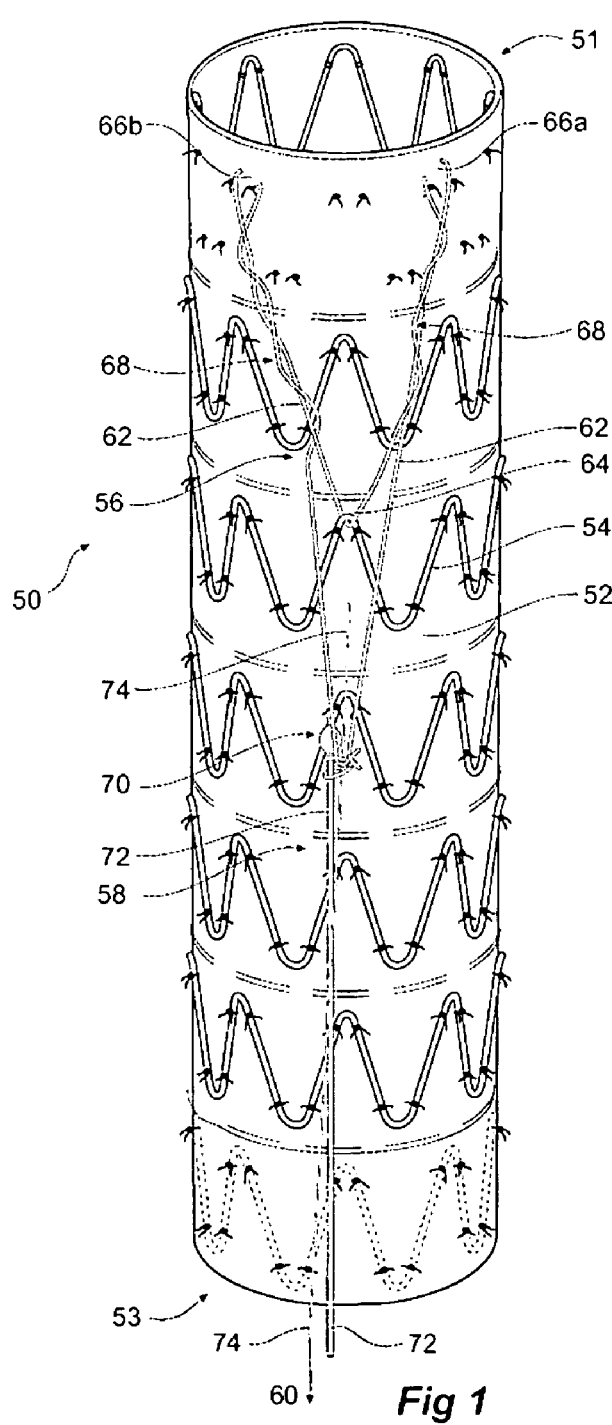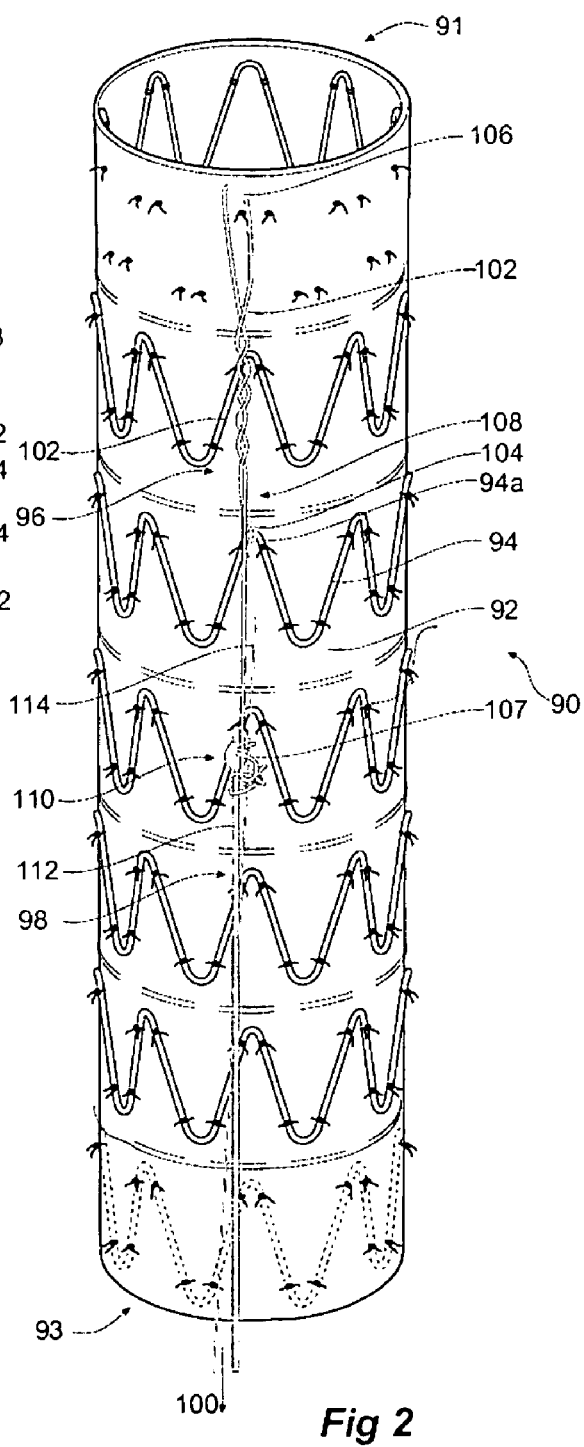
Fig 1
Fig 2

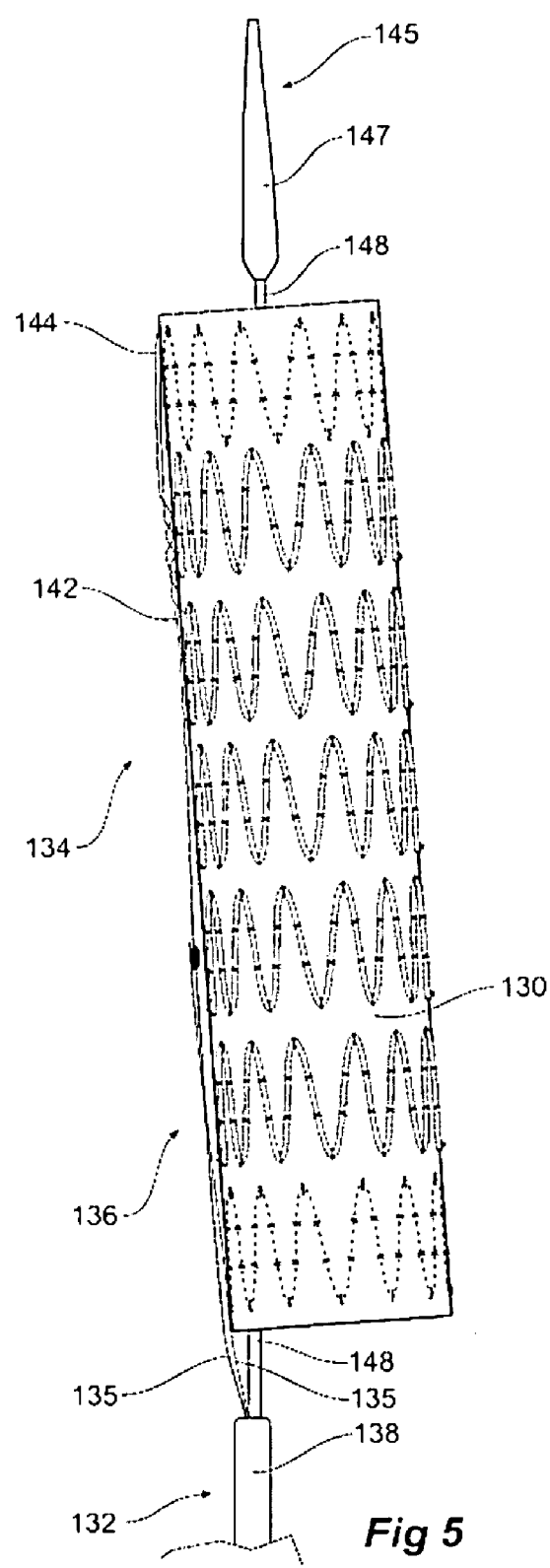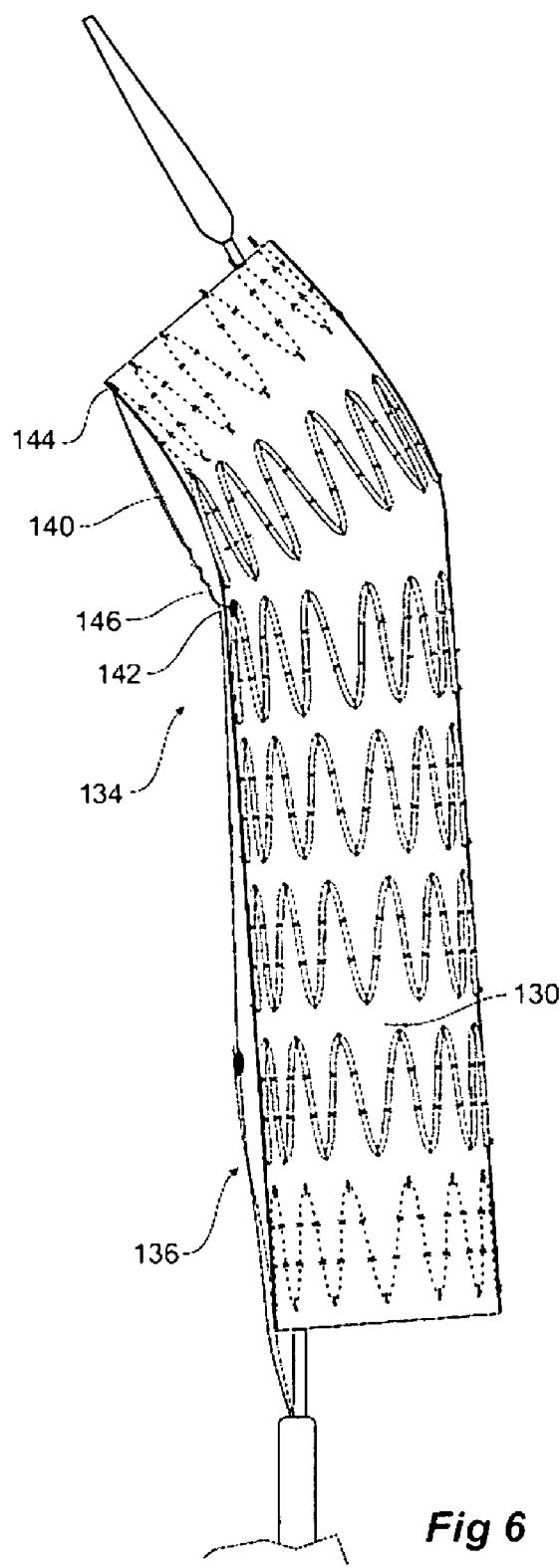

CURVE FORMING APPARATUS AND CURVABLE STENT GRAFT

CROSS-REFERENCE TO RELATED APPLICATIONS

This application claims priority of provisional application Ser. No. 61/065,329, filed Feb. 11, 2008 and provisional application Ser. No. 61/065,535, filed Feb. 13, 2008.

TECHNICAL FIELD

This invention relates to a medical device and more particularly to an endovascular device to be placed into curved portions of the vasculature of a person or animal.

The invention will generally be discussed in relation to the endovascular placement of a stent graft into the thoracic arch of a patient but the invention is not so limited and may be applied to other portions of the vasculature or other body vessels.

BACKGROUND ART

Prostheses for the repair of vascular defects, including for example vascular aneurysms, are well known in the art. A common prosthesis for treatment of such a medical condition is a stent-graft.

Prostheses of this type are typically deployed endoluminally through a vein or artery adjacent a surface of a patient, aortic prostheses, for example, being commonly fed through the femoral artery. A generally accepted method of deployment involves the location of a guide wire along the path to be followed by the introducer assembly, up to the site in the vasculature to be treated. Once the guide wire is in place, a series of catheters is advanced along the guide wire, finally with the introduction of a catheter assembly which carries the stent or stent-graft to be fitted. The catheters have sufficient trackability to follow the guide wire along the curves and turns of the patient's vasculature and some can also curve sufficiently so as to be able to fit a stent-graft, for example, into a highly curved vessel such as the aortic arch.

Even though such a procedure is possible into the aortic arch, it is mired in difficulties as a result of the tight curvature of the aorta in this location. One such difficulty arises in connection with the proximal end of the stent-graft, which is liable to be incorrectly fitted such that it incompletely seals around the inner wall of the aorta as a result of the curvature imparted to the stent-graft. This can lead to leakage of blood around the outside of the stent-graft and thus a less than effective treatment. Furthermore, as a result of the non-optimal placement of the stent-graft using known procedures, it is necessary to have a reasonable length of healthy vascular wall in order to provide a seal around the proximal end of the stent-graft. This limits the application of such stent-grafts, in particular for the treatment of aneurysms close to a branch vessel and to conditions where there is at least a certain length of healthy vessel wall tissue, thus making the procedure not available to treat a reasonable proportion of medical cases.

In addition, in some instances at least, a part of the proximal end of the stent-graft can remain loosely located in the vessel, leading to premature fatigue failure as well as thrombus effects.

Attempts have been made to resolve these difficulties. For instance, in the applicant's U.S. Pat. No. 6,974,471, mechanisms are described for imparting a curvature to the stent-graft at the moment of its deployment.

The deployment of stent-grafts and other devices, particularly in the aortic arch, in lumens having short necks of healthy vascular wall and other difficult pathologies also requires very precise placement of the device to ensure a good coupling to healthy tissue and in particular a coupling which has longevity and which provides a fluid-tight seal with the vessel wall. Prior art systems do allow for a certain amount of coarse re-positioning of the device. However, if the device is not fitted precisely in the correct location, the procedure may need to be repeated, for example by withdrawing the device back into its delivery introducer (where this is possible) and starting the deployment operation afresh. Repeating the procedure increases operating time, trauma to the patient and still does not guarantee a successful outcome. In some instances, it is necessary to abort the procedure.

Thus, when a stent graft is placed into a curved portion of the vasculature it is important to ensure that the sides engage the walls of the vessel with enough force to enable sealing and to prevent endoleaks and distortion of the stent graft.

DISCLOSURE OF THE INVENTION

The present invention seeks to provide an improved stent delivery arrangement and an improved implantable medical device.

In one form therefore although this may not be the only or broadest form the invention is said to reside in a stent graft delivery arrangement comprising:

a delivery device comprising a proximal end to be deployed into a patient in use and a distal end to remain outside the patient in use;

a stent graft releasably retained onto the delivery device towards the proximal end thereof, the stent graft comprising a tubular body of a biocompatible graft material and a plurality of self expanding stents therealong and the stent graft comprising a proximal end and a distal end;

a curve forming arrangement on the stent graft arranged in use to curve a portion of the stent graft by the proximal end thereof;

a pulling arrangement extending along the delivery device and releasably engaging the curve forming arrangement on the stent graft, whereby pulling on the pulling arrangement causes the curve forming arrangement on the stent graft to curve a portion of the stent graft by the proximal end thereof and the pulling arrangement can be released leaving the curve forming apparatus in place on the stent graft; wherein the curve forming arrangement includes a suture thread engaged to the stent graft at a first portion spaced from the proximal end of the stent graft, at a second position adjacent the proximal end of the stent graft, a third position releasably engageable to a pulling arrangement, and a gripping arrangement engaging the suture thread between the second position and the third position, wherein the suture thread from the first position to the second position and from the second position to the third position is twisted around itself.

Preferably, the curve forming arrangement on the stent graft arrangement comprises a suture thread engaged to the stent graft or a stent of the stent graft at a first position spaced apart from the proximal end of stent graft, extending in two directions to two second positions spaced circumferentially apart and adjacent to the proximal end of stent graft, at a third position releasably engaged to the pull wire and a gripping arrangement engaging the suture thread between the second position and the third position to prevent re-extension of the suture thread after retraction thereof.

According to another aspect of the present invention, there is provided a stent graft delivery arrangement comprising: a delivery device comprising a proximal end to be deployed into a patient in use and a distal end to remain outside the patient in use; a stent graft releasably retained onto the delivery device towards the proximal end thereof, the stent graft comprising a tubular body of a biocompatible graft material and a plurality of self expanding stents therealong and the stent graft comprising a proximal end and a distal end; a curve forming arrangement on the stent graft arranged in use to curve a portion of the stent graft by the proximal end thereof; a pulling arrangement extending along the delivery device and releasably engaging the curve forming arrangement on the stent graft, whereby pulling on the pulling arrangement causes the curve forming arrangement on the stent graft to curve a portion of the stent graft by the proximal end thereof and the pulling arrangement can be released leaving the curve forming apparatus in place on the stent graft; wherein the curve forming arrangement comprises a suture thread engaged to the stent graft or a stent of the stent graft at a first position spaced apart from the proximal end of stent graft, extending in at least two directions to at least two second positions spaced circumferentially apart and adjacent to the proximal end of stent graft, at a third position releasably engaged to the pull wire and a gripping arrangement engaging the suture thread between the second position and the third position to prevent re-extension of the suture thread after retraction thereof.

Preferably, the suture threads from the first position to each of the second positions and from the second positions to the third position respectively are twisted around each other.

Preferably, the releasable engagement of the curve forming arrangement to the pulling arrangement comprises a portion of the curve forming arrangement connected to the pull wire by a releasable fastening and a release wire engaging the releasable fastening extending to the distal end of the delivery device, whereby pulling on the release wire releases the releasable fastening thereby releasing the portion of the curve forming arrangement from the pulling arrangement.

Preferably, the pulling arrangement comprises a pull wire, a bead on the proximal end of the pull wire, a fastening arrangement distally of the bead and a release wire engaging the fastening arrangement, the release wire extending to the distal end of the deployment device, the curve forming arrangement engaging the fastening arrangement, whereby withdrawal of the release wire releases the fastening arrangement from the pull wire distal of the bead thereby releasing the curve forming arrangement.

According to another aspect of the present invention, there is provided a stent graft delivery arrangement comprising: a delivery device comprising a proximal end to be deployed into a patient in use and a distal end to remain outside the patient in use; a stent graft releasably retained onto the delivery device towards the proximal end thereof, the stent graft comprising a tubular body of a biocompatible graft material and a plurality of self expanding stents therealong and the stent graft comprising a proximal end and a distal end; a suture thread engaged to the stent graft at a first position spaced apart from the proximal end of stent graft, at a second position adjacent to the proximal end of stent graft, at a third position releasably engaged to a pulling arrangement and a gripping arrangement engaging the suture thread between the second position and the third position to prevent re-extension of the suture thread after retraction thereof; the gripping arrangement comprising the suture thread from the first position to the second position and from the second position to the third position bring twisted around each other; the pulling arrangement comprising a pull wire, a bead on the proximal end of the pull wire, a fastening arrangement distally of the bead and a release wire engaging the fastening arrangement, the release wire extending to the distal end of the deployment device, the curve forming arrangement engaging the fastening arrangement, whereby withdrawal of the release wire releases the fastening arrangement from the pull wire distal of the bead thereby releasing the curve forming arrangement; whereby pulling on the pull wire causes the suture thread to form a curved portion of the stent graft towards the proximal end thereof and wherein the pull wire can be released leaving the suture thread in place on the stent graft and the curved portion of the stent graft retained on the stent graft.

According to another aspect of the present invention, there is provided a stent graft including a tubular body of a biocompatible graft material and a plurality of self expanding stents therealong, the stent graft having a proximal end and a distal end; and a curve forming arrangement on the stent graft arranged in use to curve a portion of the stent graft by the proximal end thereof, the curve forming arrangement including a suture thread engaged to the stent graft at a first portion spaced from the proximal end of the stent graft, at a second position adjacent the proximal end of the stent graft, at a third position releasably engageable to a pulling arrangement, and a gripping arrangement engaging the suture thread between the second position and the third position, wherein the suture thread from the first position to the second position and from the second position to the third position is twisted around itself.

According to another aspect of the present invention, there is provided a stent graft comprising a tubular body of a biocompatible graft material and a plurality of self expanding stents therealong and the stent graft comprising a proximal end and a distal end; wherein the curve forming arrangement comprises a suture thread engaged to the stent graft or a stent of the stent graft at a first position spaced apart from the proximal end of stent graft, extending in at least two directions to at least two second positions spaced circumferentially apart and adjacent to the proximal end of stent graft, at a third position releasably engaged to the pull wire and a gripping arrangement engaging the suture thread between the second positions and the third position to prevent re-extension of the suture thread after retraction thereof.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

BRIEF DESCRIPTION OF THE DRAWINGS

Embodiments of the present invention are described below, by way of example only, with reference to the accompanying drawings, in which:

FIG. 1 shows a stent graft with a first form of curve forming arrangement according to an embodiment of the present invention thereon;

FIG. 2 shows a stent graft with a second form of curve forming arrangement according to an embodiment of the present invention thereon;

FIGS. 5 and 6 show the operation a curve forming arrangement according to one embodiment of the present invention.

DESCRIPTION OF THE PREFERRED EMBODIMENTS

Figure 3:
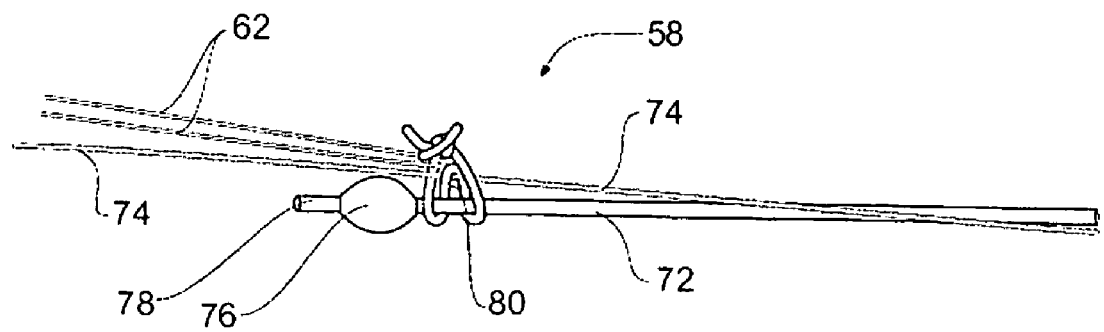
FIG. 3 shows detail of the connection between the curve forming arrangement and the pulling arrangement as show in FIG. 1.

Now looking more closely at the drawings and in particular FIG. 1 it will be seen that a stent graft 50 comprises a tubular body 52 of a biocompatible graft material. The tubular body 52 has a proximal end 51 and a distal end 53. The tubular body 52 has a plurality of self expanding stents 54 therealong. A curve forming arrangement generally shown as 56 is mounted longitudinally along the length of the tubular body 52. A pulling arrangement shown generally as 58 is connected to the curve forming arrangement 56 and the pulling arrangement 58 extends distally as shown by the arrow 60.

The curve forming arrangement 56 comprises in this embodiment a suture thread 62 engaged onto the stent graft at a first position 64 which is spaced distally from the proximal end 11 of the stent graft 10. In this embodiment the suture thread 62 is engaged to the stent graft by being passed around a bend 54*a* of a stent 54. The stent 54 is stitched to the tubular body 52. The region between the first position 64 and the proximal end 51 of the stent graft is the region in which it is desired to form a curve to more accurately conform the stent graft with a curved portion of the vasculature. The suture thread 62 is then engaged into the tubular body 52 at a pair of second positions 66*a* and 66*b* which are adjacent to the proximal end 51 of the stent graft. The suture thread 62 is then extended distally from each of the second positions 66*a* and 66*b* to engage with the pulling arrangement 58 at a third position 67. A releasable connection generally shown as 70 between the suture thread 62 and the pulling arrangement 58 will be discussed in more detail in relation to FIG. 5. The suture thread 62 includes a gripping arrangement 68 which allows the suture thread 62 to be pulled distally but not to easily move back proximally. The gripping arrangement in this embodiment comprises a portion of the suture thread 62 between the first position and the second position being twisted to a portion of the suture thread between the second position and the third position. Hence as the suture thread is moved distally the amount of suture thread between the first position and the second position is reduced thereby bending that region of the stent graft. The pulling arrangement 58 in this embodiment comprises a pull wire 72 and a release wire 74.

In some embodiments there could be more than two positions 66*a*, 66*b*, at which the suture thread 62 is passed.

The gripping arrangement means that even after the pulling arrangement 58 is released and that portion removed from the deployment device the suture thread 62 will hold the curve. In use the suture thread 62 remains in a patient connected to the stent graft after the endovascular delivery is completed.

In FIG. 1 the suture thread 64 is shown wrapped around the stent 54, at a peak between two of the struts thereof. It is also envisaged that the suture thread 64 could be knotted or otherwise tied to the strut and in some cases to the graft material itself.

The pulling arrangement 58 is shown in more detail in FIG. 3. The pull wire 72 has a bead 76 welded to its proximal end 78 and a knot 80 is formed onto the pull wire just distal of the bead 76. The knot is locked in place with the release wire 74 in such a manner that removal of the release wire 74 from the knot 80 releases the knot from the pull wire 72. The suture thread 62 is engaged into the knot 80 and when the knot is released from the pull wire 72 it remains fastened to the suture thread 62. Other methods of releasably connecting the pull wire to the suture thread may also be used.

FIG. 2 shows an further embodiment of curve forming apparatus and pulling arrangement according to the present invention. In FIG. 2 it will be seen that a stent graft 90 comprises a tubular body 92 of a biocompatible graft material. The tubular body 92 has a proximal end 91 and a distal end 93. The tubular body 92 has a plurality of self expanding stents 94 therealong. A curve forming arrangement generally shown as 96 is mounted longitudinally along the length of the tubular body 92. A pulling arrangement shown generally as 98 is connected to the curve forming arrangement 96 and the pulling arrangement 98 extends distally as shown by the arrow 100.

The curve forming arrangement 96 comprises in this embodiment a suture thread 102 engaged onto the stent graft at a first position 104 which is spaced distally from the proximal end 91 of the stent graft 90. In this embodiment the suture thread 102 is engaged to the stent graft by being passed around a bend 94*a* of a stent 94. The region between the first position 104 and the proximal end 91 is the region in which it is desired to form a curve to more accurately conform the stent graft with a curved portion of the vasculature. The suture thread 102 is then engaged into the tubular body 92 at a second position 106 which is adjacent to the proximal end 91 of the stent graft. The suture thread 102 is then extended distally from the second position 106 to engage with the pulling arrangement 98 at a third position 107. The gripping arrangement in this embodiment comprises a portion of the suture thread 102 between the second position and the third position the being twisted around the same suture thread in its extent between the first position and the second position. Hence as the suture thread is moved distally the amount of suture thread between the first position and the second position is reduced thereby bending that region of the stent graft. There is sufficient friction between the suture threads in the twisted together section to prevent re-extension after retraction. A releasable connection generally shown as 110 between the suture thread 102 and the pulling arrangement 98 will be discussed in more detail in relation to FIG. 4. The pulling arrangement 98 in this embodiment comprises a pull wire 112 and a release wire 114.

Figure 4:
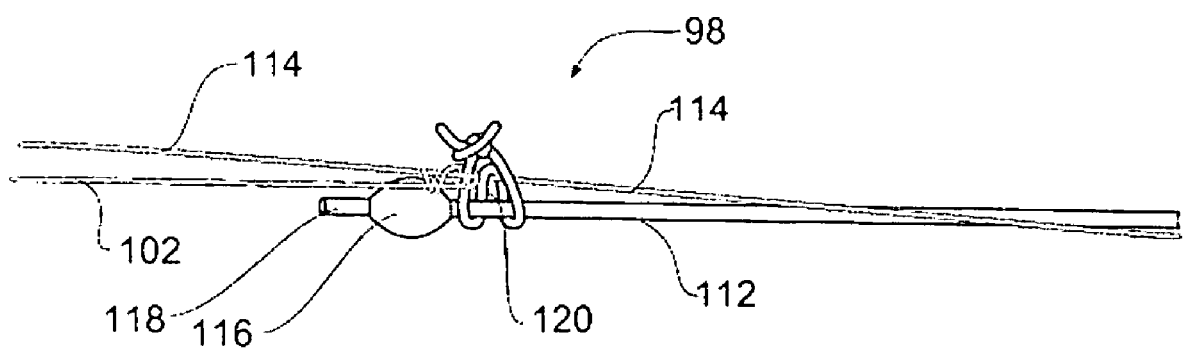
FIG. 4 shows detail of the connection between the curve forming arrangement and the pulling arrangement as show in FIG. 2.

The pulling arrangement 98 is shown in more detail in FIG. 4. The pull wire 112 has a bead 116 welded to its proximal end 118 and a knot 120 is formed onto the pull wire just distal of the bead 116. The knot is locked in place with the release wire 114 in such a manner that removal of the release wire 114 from the knot 120 releases the knot from the pull wire 112. The suture thread 102 is engaged into the knot 120 and when the knot is released from the pull wire 112 it remains fastened to the suture thread 102.

FIGS. 5 and 6 show the operation a curve forming arrangement according to one embodiment of the present invention.

In FIGS. 5 and 6 a stent graft 130 is releasably retained to a delivery device 132 and in these drawings is shown in an expanded state after a sheath (not shown) has been retracted.

The delivery device 132 comprises a proximal end 145 to be deployed into a patient in use and a distal end (not shown) to remain outside the patient in use. The proximal end 145 includes a nose cone dilator 147 mounted onto a guide wire catheter 148. The stent graft 130 is positioned coaxially around the guide wire catheter and releasably fastened to it by retention means (not shown). The delivery device 123 also includes a deployment catheter 138 which extends to a handle (not shown) at the distal end of the delivery device.

A curve forming arrangement generally shown as 134 is mounted longitudinally along the length of the stent graft 130 and pulling arrangement shown generally as 136 is connected to the curve forming arrangement 134 and the pulling arrangement 136 extends distally. The pull wire 135 and release wire 137 of the pulling arrangement 136 are received into a lumen of the deployment catheter 138 of the delivery device 132.

The curve forming arrangement 134 includes a suture thread 140 fastened to the stent graft at a first position 142 and passing through a second position 144, then twisted around the thread between the first and second positions adjacent to the first position and then to the pulling arrangement 136. As can be seen in FIG. 6 when the pull wire 135 is pulled the length of suture thread 140 between the first position 142 and the second position 144 is reduced and as the pulling force is to one side of the stent graft a curve in the stent graft is formed.

Figure 7:
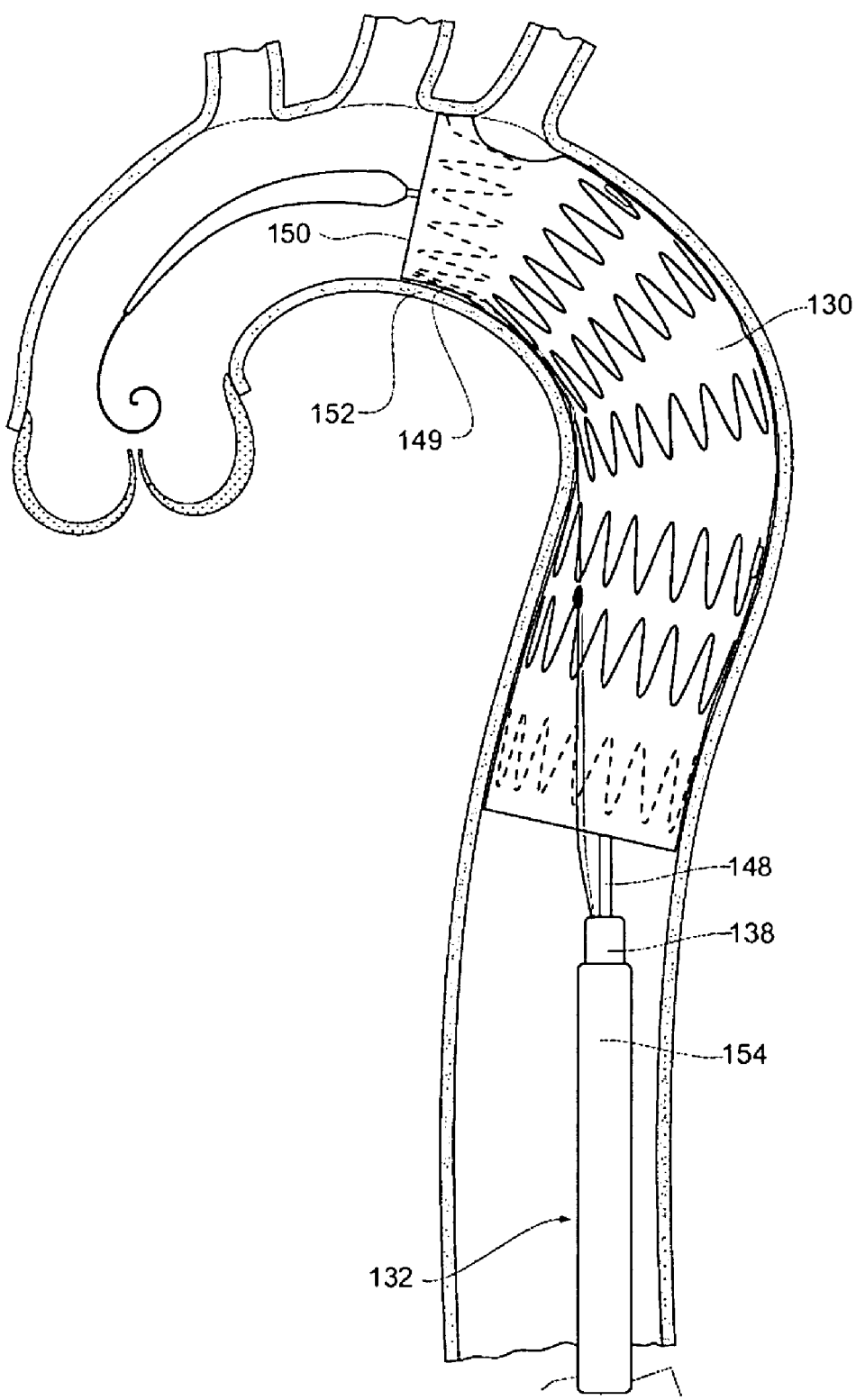
FIG. 7 shows schematically the thoracic arch of a patient with a stent graft according to an embodiment of the present invention deployed therein.

FIG. 7 shows schematically the thoracic arch of the aorta of a patient with a stent graft according of a type as disclosed above deployed therein.

It will be noted that the sheath 154 of the delivery device 132 has been retracted and the stent graft 130 has expanded out to the wall of the aorta. It will also be noted that the stent graft 130 is curved to conform with the shape of the vasculature by the use of the apparatus of the present invention and in particular that the inside portion 148 of the proximal end 150 is held against the inside curve of the thoracic aorta 152 thereby giving a good seal.

What is claimed is:

1. A stent graft delivery arrangement comprising:
a delivery device comprising a proximal end to be deployed into a patient in use and a distal end to remain outside the patient in use;
a stent graft releasably retained onto the delivery device towards the proximal end thereof, the stent graft comprising a tubular body of a biocompatible graft material and a plurality of self expanding stents therealong and the stent graft comprising a proximal end and a distal end;
a curve forming arrangement on the stent graft arranged in use to curve a portion of the stent graft by the proximal end thereof;
a pulling arrangement extending along the delivery device and releasably engaging the curve forming arrangement on the stent graft, whereby pulling on the pulling arrangement causes the curve forming arrangement on the stent graft to curve a portion of the stent graft by the proximal end thereof and the pulling arrangement can be released leaving the curve forming apparatus in place on the stent graft;
wherein the curve forming arrangement comprises a suture thread engaged to the stent graft or a stent of the stent graft at a first position spaced from the proximal end of the stent graft, extending in at least two directions to at least two second positions spaced circumferentially apart and adjacent to the proximal end of stent graft, at a third position releasably engaged to the pulling arrangement and a gripping arrangement engaging the suture thread between the second position and the third position to prevent re-extension of the suture thread after retraction thereof.

2. A stent graft delivery arrangement as in claim 1 wherein the gripping arrangement comprises the suture threads from the first position to each of the second positions and from the second positions to the third position respectively being twisted around each other.

3. A stent graft delivery arrangement as in claim 1 wherein the releasable engagement of the curve forming arrangement to the pulling arrangement comprises a portion of the curve forming arrangement connected to the pulling arrangement by a releasable fastening and a release wire engaging the releasable fastening extending to the distal end of the delivery device, whereby pulling on the release wire releases the releasable fastening thereby releasing the portion of the curve forming arrangement from the pulling arrangement.

4. A stent graft delivery arrangement as in claim 3 wherein the pulling arrangement comprises a pull wire, a bead on the proximal end of the pull wire, a fastening arrangement distally of the bead and a release wire engaging the fastening arrangement, the release wire extending to the distal end of the deployment device, the curve forming arrangement engaging the fastening arrangement, whereby withdrawal of the release wire releases the fastening arrangement from the pull wire distal of the bead thereby releasing the curve forming arrangement.

5. A stent graft delivery arrangement comprising:
a delivery device comprising a proximal end to be deployed into a patient in use and a distal end to remain outside the patient in use;
a stent graft releasably retained onto the delivery device towards the proximal end thereof, the stent graft comprising a tubular body of a biocompatible graft material and a plurality of self expanding stents therealong and the stent graft comprising a proximal end and a distal end;
a curve forming arrangement on the stent graft arranged in use to curve a portion of the stent graft by the proximal end thereof;
a pulling arrangement extending along the delivery device and releasably engaging the curve forming arrangement on the stent graft, whereby pulling on the pulling arrangement causes the curve forming arrangement on the stent graft to curve a portion of the stent graft towards the proximal end thereof and the pulling arrangement can be released leaving the curve forming apparatus in place on the stent graft;
wherein the curve forming arrangement on the stent graft comprises a suture thread engaged to the stent graft at a first position spaced apart from the proximal end of the stent graft, at a second position adjacent to the proximal end of the stent graft, at a third position releasably engaged to the pulling arrangement and a gripping arrangement engaging the suture thread between the second position and the third position to prevent re-extension of the suture thread after retraction thereof; and
wherein the gripping arrangement comprises the suture thread from the first position to the second position and from the second position to the third position being twisted around each other.

6. A stent graft delivery arrangement as in claim 5 wherein the suture thread between the second position and the third position is engaged into the tubular body to provide the gripping arrangement.

7. A stent graft delivery arrangement as in claim 5 wherein the curve forming arrangement on the stent graft arranged comprises a suture thread engaged to the stent graft or a stent of the stent graft at a first position spaced apart from the proximal end of stent graft, extending in at least two directions to at least two second positions spaced circumferentially apart and adjacent to the proximal end of the stent graft, at a third position releasably engaged to the pull wire and a gripping arrangement engaging the suture thread between the second position and the third position to prevent re-extension of the suture thread after retraction thereof.

8. A stent graft delivery arrangement as in claim 5 wherein the suture thread between the or each of the second positions and the third position is engaged into the tubular body.

9. A stent graft comprising a tubular body of a biocompatible graft material and a plurality of self expanding stents therealong and the stent graft comprising a proximal end and a distal end; wherein a curve forming arrangement comprises a suture thread engaged to the stent graft or a stent of the stent graft at a first position spaced apart from the proximal end of the stent graft, extending in at least two directions to at least two second positions spaced circumferentially apart and adjacent to the proximal end of the stent graft, at a third position releasably engaged to the pull wire and a gripping arrangement engaging the suture thread between the second position and the third position to prevent re-extension of the suture thread after retraction thereof.

10. A stent graft including a tubular body of a biocompatible graft material and a plurality of self expanding stents therealong, the stent graft having a proximal end and a distal end; and a curve forming arrangement on the stent graft arranged in use to curve a portion of the stent graft towards the proximal end thereof, the curve forming arrangement including a suture thread engaged to the stent graft at a first portion spaced from the proximal end of the stent graft, at a second position adjacent the proximal end of the stent graft, at a third position releasably engageable to a pulling arrangement, and a gripping arrangement engaging the suture thread between the second position and the third position, wherein the suture thread from the first position to the second position and from the second position to the third position is twisted around itself.

* * * * *